(12) United States Patent
Meder et al.

(10) Patent No.: US 11,953,673 B2
(45) Date of Patent: Apr. 9, 2024

(54) OPTICAL COUPLING, ENDOSCOPY ARRANGEMENT AND CORRESPONDING USE

(71) Applicant: Scholly Fiberoptic GmbH, Denzlingen (DE)

(72) Inventors: Wolfgang Meder, Glottertal (DE); Martin Hercher, Algolsheim (FR)

(73) Assignee: Schölly Fiberoptic GmbH, Denzlingen (DE)

( * ) Notice: Subject to any disclaimer, the term of this patent is extended or adjusted under 35 U.S.C. 154(b) by 0 days.

(21) Appl. No.: 17/590,868

(22) Filed: Feb. 2, 2022

(65) Prior Publication Data
US 2022/0244522 A1    Aug. 4, 2022

(30) Foreign Application Priority Data
Feb. 4, 2021  (DE) .......................... 102021102653.9

(51) Int. Cl.
| G02B 23/24 | (2006.01) |
| A61B 1/00  | (2006.01) |
| G02B 6/42  | (2006.01) |

(52) U.S. Cl.
CPC ...... G02B 23/2476 (2013.01); A61B 1/00126 (2013.01); G02B 6/4292 (2013.01); G02B 23/2469 (2013.01)

(58) Field of Classification Search
CPC ............ G02B 23/2476; G02B 23/2469; G02B 6/4292; A61B 1/00126; A61B 1/00117; A61B 1/00112; A61B 1/01
See application file for complete search history.

(56) References Cited

U.S. PATENT DOCUMENTS

| 2010/0113942 A1* | 5/2010 | Eberle ................ G02B 6/3874 600/478 |
| 2023/0091208 A1* | 3/2023 | Lai .......................... A61B 1/05 |

FOREIGN PATENT DOCUMENTS

| CN | 103118583 A   | * | 5/2013 | ............ A61B 17/24 |
| CN | 105581766 B   | * | 8/2019 | ........ A61B 1/00126 |
| CN | 110115599 A   | * | 8/2019 | ............. A61B 8/12 |
| DE | 8709993       |   | 9/1987 | |
| WO | WO-2013127919 A2 | * | 9/2013 | ........ A61B 1/00126 |
| WO | WO-2015111413 A1 | * | 7/2015 | ........ A61B 1/00126 |
| WO | WO-2015127265 A1 | * | 8/2015 | ........ A61B 1/00082 |
| WO | WO-2018108396 A1 | * | 6/2018 | ........ A61B 1/00126 |

* cited by examiner

*Primary Examiner* — Michelle R Connelly
*Assistant Examiner* — Mary A El-Shammaa
(74) *Attorney, Agent, or Firm* — Volpe Koenig

(57) ABSTRACT

An optical coupling having a coupling part and a mating coupling part which are detachably connected to one another is provided, a connection element being arranged on the coupling part and a fitting mating connection element being arranged on the mating coupling part. These connection elements together form a common optical channel, and the mating connection element is arranged with play in the mating coupling part and without play in the coupling part.

11 Claims, 3 Drawing Sheets

OPTICAL COUPLING, ENDOSCOPY ARRANGEMENT AND CORRESPONDING USE

INCORPORATION BY REFERENCE

The following documents are incorporated herein by reference as if fully set forth: German Patent Application No. 10 2021 102 653.9, filed Feb. 4, 2021.

TECHNICAL FIELD

The invention relates to an optical coupling having a coupling part and a mating coupling part which are detachably connected to one another, a connection element being arranged on the coupling part and a fitting mating connection element being arranged on the mating coupling part, these connection elements forming an optical channel in relation to one another. Such an optical coupling is known.

The invention also relates to an endoscopy arrangement having an optical coupling. Such an endoscopy arrangement is known.

The invention also relates to the use of an optical coupling in endoscopy. Such a use is known.

BACKGROUND

Optical couplings of this type are known and are used, for example in endoscopes, to connect a light source or a light guide to a corresponding light guide path in an endoscope.

The invention is based on the object of aligning the transition between the two partial optical paths, for example between the connection element and the mating connection element, as accurately as possible, for example in order to prevent unnecessary instances of heat development, heat losses or—in the case of image guidance—optical imaging aberrations. The invention is further based on the object of minimizing the sum of the manufacturing tolerances of the parts, and of simplifying the mechanical structure and the assembly of the components. The objects are achieved by the use of one or more of the features described herein. Advantageous embodiments are described below and in the claims.

To achieve these objects, the invention provides in the case of an optical coupling of the type set forth at the outset, that the mating connection element is arranged with play in the mating coupling part and without play in the coupling part. What this achieves is that the coupling part aligns the connection element and the mating connection element with respect to one another such that manufacturing tolerances have less influence. Over determination of the alignment is consequently rendered avoidable.

An advantageous embodiment according to the invention can provide for the connection element to be in the form of a fiber cone. Alternatively or additionally, provision can be made for the mating connection element to be in the form of a fiber socket. Alternatively or additionally, provision can be made for the coupling part to be in the form of a connection socket. Alternatively or additionally, provision can be made for the mating coupling part to be in the form of a fiber connection socket. Thus, different functions of the parts can be realized and specific structural realizations can be provided.

In a further advantageous embodiment, provision can be made for a guide surface to be formed on the coupling part and to arrange the connection element and the mating connection element in relation to one another. Consequently, aligning the mating connection element with the coupling part is easily attainable.

A cylindrical guide surface is particularly expedient. Consequently, it is possible to attain an optimal arrangement between connection element and mating connection element. Consequently, it is furthermore possible to minimize the sum of the manufacturing tolerances, and mechanical structure and the assembly of the components can be simplified. In particular, it is advantageous here that the guide surface for the connection element and the mating connection element can be produced in one work step.

In a further advantageous embodiment, provision can be made for the mating coupling part to be screwed to a main body by way of a fastening thread. Consequently, it is possible to obtain a simple and detachable connection between the main body and the mating coupling part.

In a further advantageous embodiment, provision can be made for the mating coupling part to be screwed to the coupling part by way of a coupling thread. Consequently, it is possible to obtain a simple and detachable connection between the coupling part and the mating coupling part.

In a further advantageous embodiment, provision can be made for a breakaway torque of the fastening thread to be greater than a breakaway torque of the coupling thread. Consequently, by using a smaller breakaway torque or torque, the mating coupling part can be separated from the coupling part without the mating coupling part being separated from the main body. Consequently, the manufacturing or installation method can moreover be simplified.

Such a selective disconnection is required, for example, during the assembly or during the grinding of optical guides such as fiber guides or optical fibers, for example.

The magnitude of the breakaway torques can be defined by the diameters and the pitches of the threads. By way of example, the fastening thread can take the shape of a fine thread as M8×0.5 with a small pitch. The coupling thread can take the shape of a fine thread, for example, as M9×1.0 with a greater pitch. The diameters of the fastening threads and the coupling threads may be the same, with a different pitch of the threads possibly being required in such a case.

In a further advantageous embodiment, provision can be made for the mating connection element to have a channel opening which narrows in the direction of the connection element. Consequently, the positioning of optical elements, for example fiber guides or optical fibers, within the channel opening and in the direction of the connection element can be simplified. By way of example, the channel opening can take the shape of a trumpet. What is likewise advantageous here is that friction between the optical elements, for example the fiber guides, and the mating connection element can be reduced. Consequently, it is possible to prevent damage to the optical elements. A further advantage that may arise here is that the assembly, for example of the optical fibers in the mating connection element, is simplified.

In a further advantageous embodiment, provision can be made for an optical guide to be arranged in the connection element. Provision can be made for the optical guide to be connected to the connection element in integrally bonded fashion and/or in frictionally connected fashion. By way of example, the optical guide could be in the form of optical fibers or in the form of a glass part, for example a glass lens. By way of example, the integral bond can be obtained by means of an adhesive bond or by soldering. Consequently, optimal positioning of the optical guide and, additionally, sealing can be ensured.

Alternatively or additionally, provision can be made for an optical guide to be arranged in the mating connection element. Provision can be made for the optical guide to be connected to the mating connection element in integrally bonded fashion and/or in frictionally connected fashion. By way of example, the integral bond can be obtained by means of an adhesive bond or by soldering. Consequently, optimal positioning of the optical guide in relation to the mating connection element can be ensured.

In a further advantageous embodiment, provision can be made for the optical guide to be a light guide. Consequently, an optimal application can be ensured. Consequently, light losses or heat losses can furthermore be reduced during a light transmission by virtue of an accurate alignment without a gap being attainable.

Alternatively or additionally, provision can be made for the optical guide to be an image guide. Consequently, an optimal application can be ensured. Consequently, imaging aberrations can furthermore be reduced during an image transmission by virtue of an accurate alignment without a gap being attainable.

In a further advantageous embodiment, provision can be made for a glass body to be arranged in the connection element and a fiber guide to be arranged in the mating connection element. Consequently, optimal positioning between the glass body and the fiber guide can be ensured. In this context, it is advantageous if the glass body and the connection element are tightly connected. Consequently, it is possible to prevent an unwanted ingress or egress of liquid. It generally is the case that the fiber guide comprises a bundle of optical fibers which, although densified and adhesively bonded, have not been hermetically sealed, and so moisture can penetrate between the individual optical fibers.

The invention moreover relates to an endoscopy arrangement comprising an optical coupling having the features according to the invention, for example wherein the optical channel is used for a light transmission and/or an image transmission. Consequently, a reduction in manufacturing tolerances or an increase in product quality can be attained in a preferred application.

In an advantageous embodiment, provision can be made for the coupling part to be arranged proximally within the endoscopy arrangement. What can be advantageous here is that the part with play is not arranged directly at the mating coupling of the optical cable.

Alternatively, provision can be made for the coupling part to be arranged distally. Consequently, a structural alternative can be provided.

By way of example, proximal may denote proximity to the surgeon, for example the physician, or distance from the examination object (e.g., patient); by way of example, distal may denote proximity to the examination object, for example the patient.

The invention moreover relates to the use in endoscopy of an optical coupling having the features according to the invention, for example for light transmission. Consequently, it is possible to attain exact positioning of optical guides or an improved structure.

BRIEF DESCRIPTION OF THE DRAWINGS

The invention will now be described in more detail on the basis of a few exemplary embodiments, but is not restricted to these few exemplary embodiments. Further variants of the invention and exemplary embodiments arise from combining the features of individual claims or of a plurality of claims among themselves and/or with individual features or a plurality of features of the exemplary embodiments and/or the above-described variants of apparatuses according to the invention.

In the figures.

DETAILED DESCRIPTION

Figure 1:
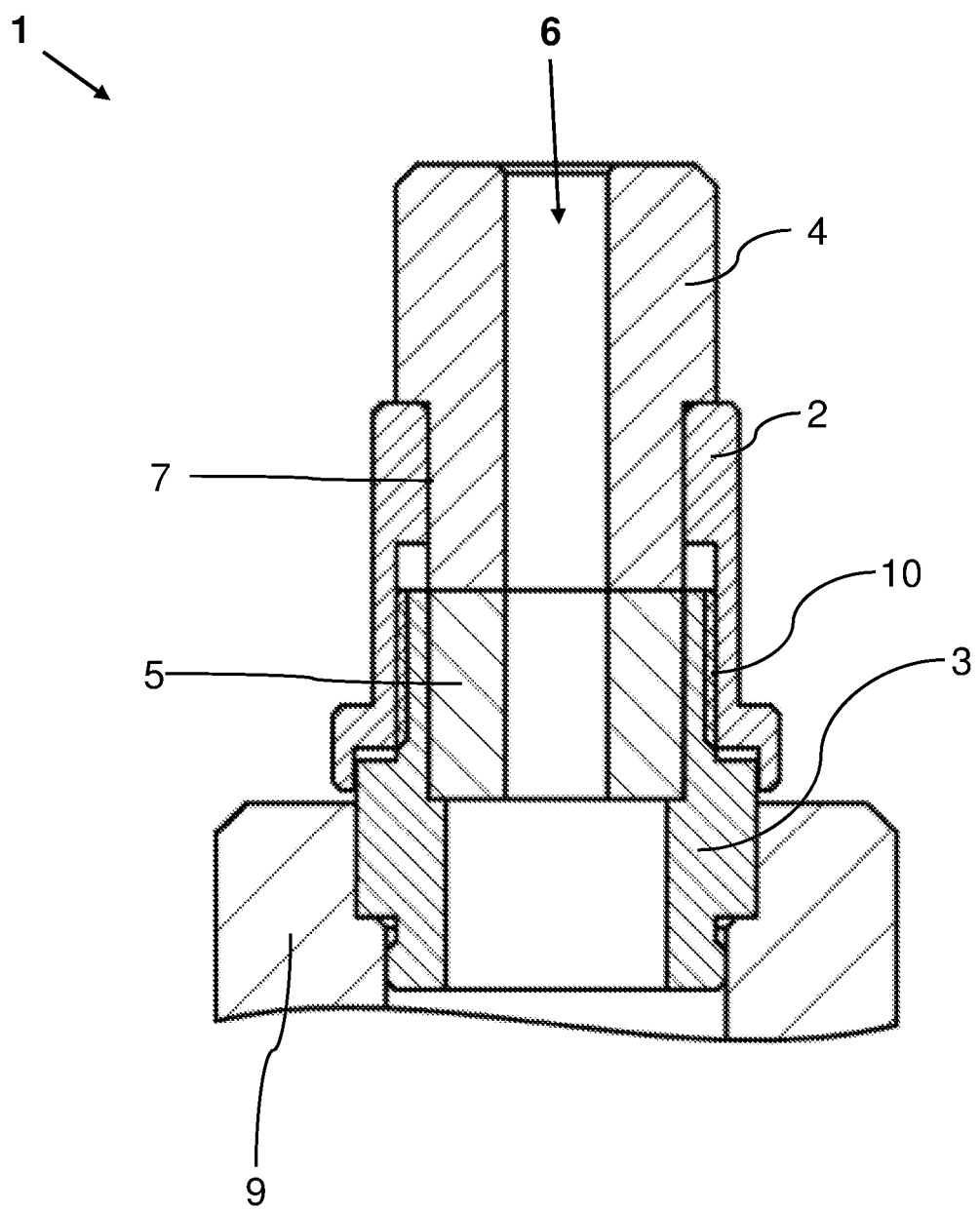
FIG. 1 shows an optical coupling according to the prior art.

In the following description of various exemplary embodiments of the invention, elements that correspond in terms of their function receive corresponding reference numerals, even in the case of a deviating design or shape.

FIG. 1 shows an optical coupling according to the prior art.

The optical coupling 1 comprises a coupling part 2, a mating coupling part 3, a connection element 4 and a mating connection element 5.

The optical coupling 1 is fastened to a main body 9. Fastening can be achieved by means of a thread or by means of welding, for example.

The optical coupling 1 has an optical channel 6, which is continuous through a bore of the connection element 4, through a bore of the mating connection element 5, and through a bore of the mating coupling part 3.

The mating coupling part 3 is screwed to the coupling part 2 by way of a coupling thread 10.

The diameters of the bore of the connection element 4 and of the bore of the mating connection element 5 should be the same.

A guide surface 7 takes shape on the coupling part 2 and is in direct contact with the connection element 4. This guide surface 7 is cylindrical.

The mating connection element 5 and the connection element 4 are arranged in relation to one another. The positioning of these two elements is determined by the contact between connection element 4 and coupling part 2, in particular the guide surface 7, the contact between coupling part 2 and mating coupling part 3, and the contact between mating coupling part 3 and mating connection element 5. Accordingly, three or more manufacturing tolerances have to be taken into account in this example, these manufacturing tolerances adding up and leading to a poor (non-optimal) alignment of the end faces of connection element 4 and mating connection element 5, and as a consequence possibly leading to more rejection of material or components during a quality analysis.

The mating coupling part 3 has a shoulder on which the mating connection element 5 is seated.

Figure 2:
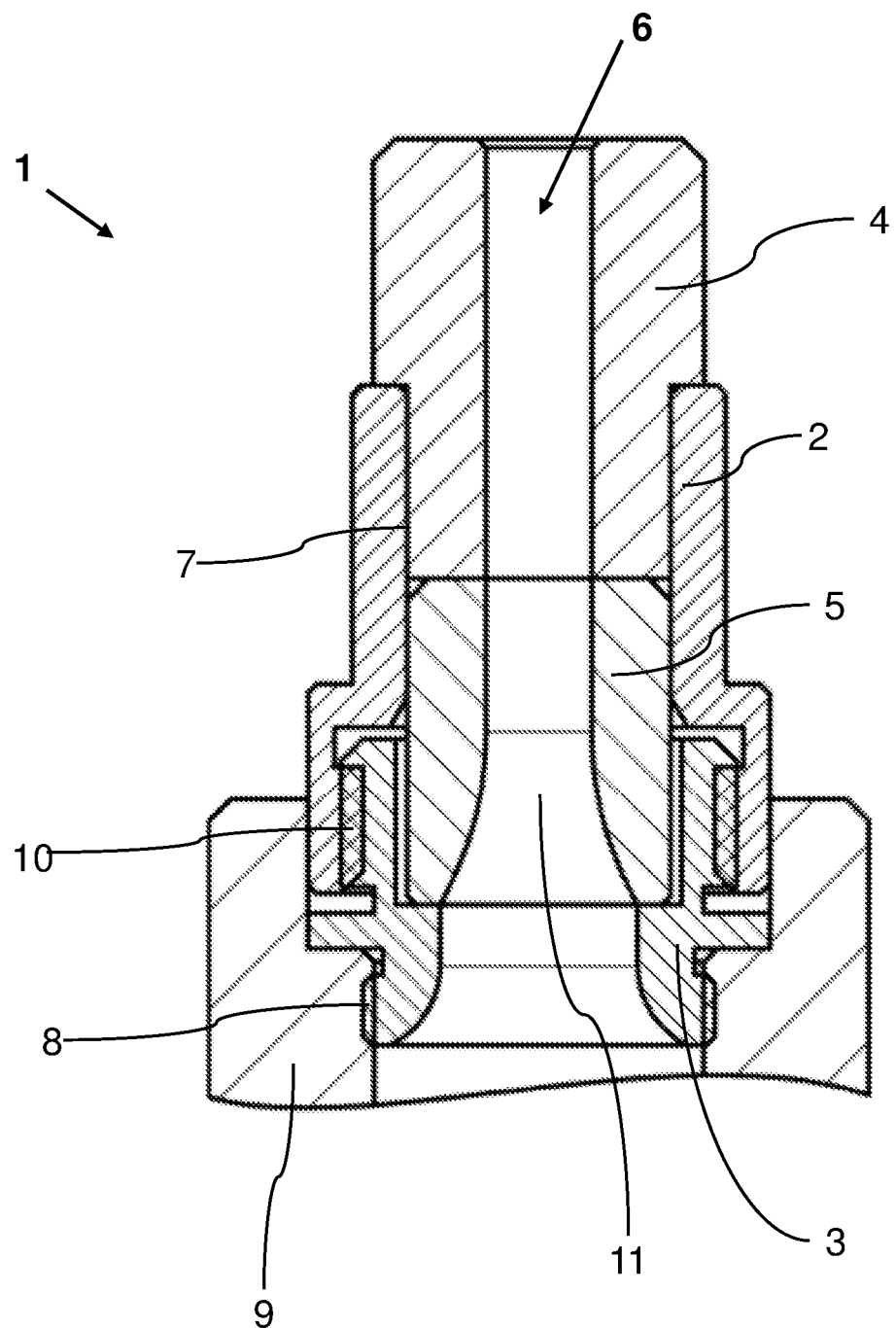
FIG. 2 shows an optical coupling according to this invention.

FIG. 2 shows an optical coupling according to this invention.

The optical coupling 1 comprises a coupling part 2, a mating coupling part 3, a connection element 4 and a mating connection element 5.

The connection element 4 may be in the form of a fiber cone. The mating connection element 5 may be in the form of a fiber socket. The coupling part 2 may be in the form of a connection socket. The mating coupling part 3 may be in the form of a fiber connection socket.

The optical coupling 1 is fastened to a main body 9. The main body 9 belongs to an endoscope shaft or an endoscope. Fastening is achieved by means of a fastening thread 8. The fastening thread 8 takes shape between the mating coupling part 3 and the main body 9.

The optical coupling 1 has an optical channel 6, which is continuous through a bore of the connection element 4, through a bore of the mating connection element 5, and through a bore of the mating coupling part 3.

The mating connection element 5 is arranged without play in the coupling part 2 and the mating connection element 5 is arranged with play in the mating coupling part 3. In this context, without play means that there is direct contact between the mating connection element 5 and the coupling part 2 transversely to the axial direction. In this context, with play means that there is no direct contact between the mating connection element 5 and the mating coupling part 3 transversely to the axial direction.

The mating coupling part 3 is screwed to the coupling part 2 by way of a coupling thread 10.

The breakaway torque of the fastening thread 8 is greater than the breakaway torque of the coupling thread 10. The magnitude of the breakaway torques can be defined by way of the diameters and the pitches of the threads. By way of example, the fastening thread 8 can take the shape of a metric fine thread M8×0.5. By way of example, the coupling thread 10 can take the shape of a metric fine thread M9×1.0. This can ensure selective opening of screwed together parts during the assembly and during manual activities, or this can prevent damage to fiber guides, for example.

A guide surface 7 takes shape on the coupling part 2 and is in direct contact with the connection element 4 and the mating connection element 5. The guide surface 7 is cylindrical. The guide surface 7 aligns the connection element 4 and the mating connection element 5 in relation to one another. The guide surface 7 may be conical in another exemplary embodiment.

The connection element 4 and the mating connection element 5 are arranged in relation to one another. The positioning of these two elements is determined by the contact between connection element 4 and coupling part 2 and the contact between coupling part 2 and mating connection element 5. Accordingly, two or more manufacturing tolerances should be considered in this example, and consequently fewer tolerances need to be considered than in the example of FIG. 1, which describes the prior art. In this respect, the example of FIG. 2 represents an improvement over the example of FIG. 1, for example in relation to mechanical manufacturing and positioning with a precise fit. Optimal positioning between connection element 4 and mating connection element 5, and consequently between the optical guides situated in the optical channel, is desirable, for example to prevent light losses or excessive development of heat.

The connection element 4 has a shoulder which is seated on the coupling part 2. There is an integrally bonded connection between the connection element 4 and the coupling part 2. The integral bond is ensured by a welded seam and is consequently hermetically sealed. The integral bond can be attained by way of an adhesive in another exemplary embodiment. What is advantageous here is that an ingress of liquid into, or an egress of liquid from, the optical coupling can be prevented.

The mating coupling part 3 has a shoulder on which the mating connection element 5 is seated.

There is an integrally bonded connection between the main body 9 and the coupling part 2. The integral bond is ensured by a welded seam and is consequently welded in hermetically sealed fashion. The integral bond can be attained by way of an adhesive in another exemplary embodiment. What is likewise advantageous here is that an egress of liquid from, or an ingress of liquid into, the optical coupling can be prevented.

An optical guide (not illustrated in FIG. 2) is arranged in the connection element 4. A fiber guide (not illustrated in FIG. 2) is arranged in the mating connection element 5.

By way of example, the fiber guide can be a light guide or an image guide or a combination of both. The fiber guide may comprise a bundle of optical fibers.

The mating connection element 5 has a channel opening 11, which narrows in the direction of the connection element 4. The shape of the channel opening 11 may be described as trumpet shaped. In this way, it is possible to attain improved positioning of for example fiber guides and the associated optical fibers, and potential damage due to friction between the fiber guides and the surface of the mating connection element 5 can be reduced. The optical fibers of the fiber guide in the mating connection element 5 are densified and adhesively bonded at the contact point to the optical guide in the connection element 4 but are not hermetically sealed. The optical fibers may guide liquid in capillary fashion. A structure as described herein is expedient for the assembly, which contains for example the polishing of optical fibers and the adhesive bonding of optical fibers.

In the case illustrated in FIG. 2, provision is made for the main body 9 to be connected to an endoscope shaft (not illustrated in FIG. 2) and for the light source 13 (not illustrated in FIG. 2) to act from above and for the light-guide cable 14 (not illustrated in FIG. 2) to be guided to the connection element 4 from above. The light-guide cable 14 has a mating coupling (not illustrated in FIG. 2), which is placed directly on the optical coupling 1 and which is detachably connected to the connection element 4. A glass body (not illustrated in FIG. 2) is arranged in the connection element 4. The connection between the glass body and the connection element 4 is hermetically sealed, and so liquid ingress or liquid egress can be prevented. The glass body may be a glass lens. In another exemplary embodiment, the glass body may be formed from plastic. The coupling part 2 is arranged proximally in FIG. 2.

However, this is not the only option. The coupling part may be arranged distally in another exemplary embodiment. Thus, it is possible for the optical coupling 1 to be accordingly installed in reverse.

Figure 3:
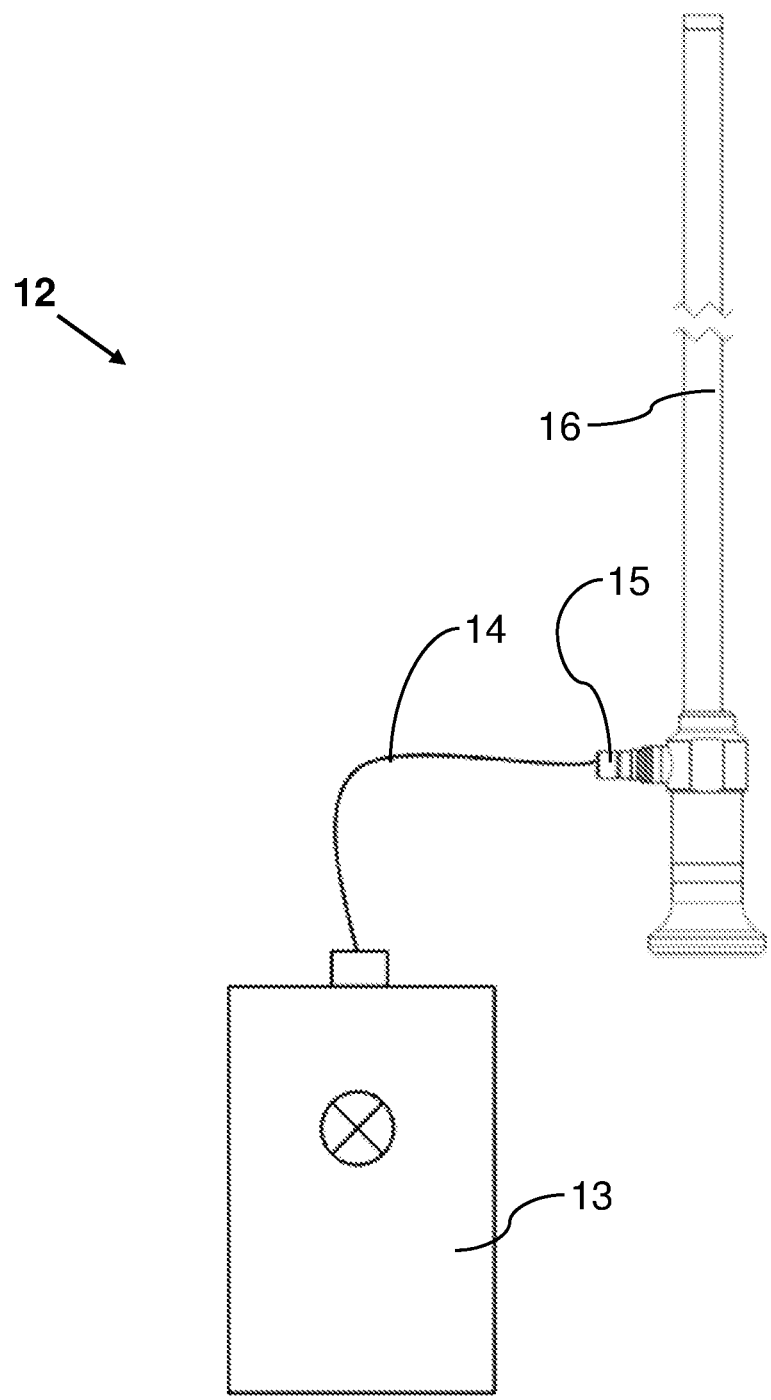
FIG. 3 shows an endoscopy arrangement.

FIG. 3 shows an endoscopy arrangement.

The endoscopy arrangement 12 comprises a light source 13 which is connected to an endoscope 16 via a light-guide cable 14. The endoscope 16 inter alia has an optical channel for light transmission.

The light-guide cable 14 is connected to the endoscope 16 by means of a light-guide connection 15.

The endoscope 16 moreover comprises an optical coupling 1 (not illustrated in FIG. 3) according to this invention and according to the claimed features.

An optical coupling having a coupling part and a mating coupling part which are detachably connected to one another is disclosed, a connection element being arranged on the coupling part and a fitting mating connection element being arranged on the mating coupling part, these connection elements together forming a common optical channel, wherein the mating connection element is arranged with play in the mating coupling part and without play in the coupling part.

LIST OF REFERENCE SIGNS

1 Optical coupling
2 Coupling part

3 Mating coupling part
4 Connection element
5 Mating connection element
6 Optical channel
7 Guide surface
8 Fastening thread
9 Main body
10 Coupling thread
11 Channel opening
12 Endoscopy arrangement
13 Light source
14 Light-guide cable
15 Light-guide connection
16 Endoscope

The invention claimed is:

1. An optical coupling (1), comprising:
a coupling part (2) and a mating coupling part (3) which are detachably connected to one another;
a connection element (4) arranged on the coupling part (2);
a mating connection element (5) arranged on the mating coupling part (3);
the connection element and the mating connection element together form a common optical channel (6);
the mating connection element (5) is arranged with play in the mating coupling part (3) and without play in the coupling part (2);
the mating coupling part (3) is configured to be screwed to a main body (9) by a fastening thread (8);
the mating coupling part (3) is screwed to the coupling part (2) by a coupling thread (10); and
a breakaway torque of the fastening thread (8) is greater than a breakaway torque of the coupling thread (10).

2. The optical coupling (1) as claimed in claim 1, wherein the connection element (4) comprises a fiber cone and the mating connection element (5) comprises a fiber socket.

3. The optical coupling (1) as claimed in claim 1, wherein a guide surface (7) is formed on the coupling part (2) and arranges the connection element (4) and the mating connection element (5) in relation to one another.

4. The optical coupling (1) as claimed in claim 1, wherein the mating connection element has a channel opening (11) which narrows in a direction of the connection element (4).

5. The optical coupling (1) as claimed in claim 1, wherein an optical guide is arranged in at least one of the connection element (4) or the mating connection element (5).

6. The optical coupling (1) as claimed in claim 5, wherein the optical guide is at least one of a light guide or an image guide.

7. The optical coupling (1) as claimed in claim 1, further comprising a glass body arranged in the connection element (4) and a fiber guide arranged in the mating connection element (5).

8. The optical coupling (1) as claimed in claim 1, wherein the coupling part (2) comprises a connection socket and the mating coupling part (3) comprises a fiber connection socket.

9. An endoscopy arrangement (12) comprising the optical coupling (1) as claimed in claim 1, and the optical connection channel (6) is configured for at least one of light transmission or image transmission.

10. The endoscopy arrangement (12) as claimed in claim 9, wherein the coupling part (2) is arranged proximally on the endoscopy arrangement.

11. The endoscopy arrangement (12) as claimed in claim 9, wherein the coupling part (2) is arranged distally.

* * * * *